United States Patent [19]
Tamegai et al.

[11] Patent Number: 5,204,888
[45] Date of Patent: Apr. 20, 1993

[54] BONE MINERAL CONTENT MEASURING APPARATUS

[75] Inventors: Toshiaki Tamegai; Kazuyuki Tamura; Shigeo Kimura; Koichi Kawamura; Shizuo Ninomiya, all of Tokyo, Japan

[73] Assignee: Aloka Co., Ltd., Tokyo, Japan

[21] Appl. No.: 628,619

[22] Filed: Dec. 14, 1990

[30] Foreign Application Priority Data

Dec. 14, 1989 [JP] Japan .................................. 1-324954
Dec. 14, 1989 [JP] Japan .................................. 1-324955
Dec. 20, 1989 [JP] Japan .................................. 1-332279

[51] Int. Cl.⁵ .............................................. G01N 23/06
[52] U.S. Cl. ...................................... 378/53; 378/54; 378/156; 378/158; 378/99
[58] Field of Search ................ 378/53, 54, 55, 415, 378/156, 157, 158, 99, 111, 56, 62, 158

[56] References Cited

U.S. PATENT DOCUMENTS

| | | | |
|---|---|---|---|
| 3,435,220 | 3/1969 | Hanken | 250/83.3 |
| 3,715,588 | 2/1973 | Rose | 250/71.5 |
| 3,974,386 | 8/1976 | Mistretta et al. | 378/111 |
| 4,528,685 | 7/1985 | Kump et al. | 378/157 |
| 4,686,695 | 8/1987 | Macovski | 378/146 |
| 4,811,373 | 3/1989 | Stein | 378/54 |
| 5,020,085 | 5/1991 | Kawara et al. | 378/99 |
| 5,040,199 | 8/1991 | Stein | 378/56 |

FOREIGN PATENT DOCUMENTS 0168090 1/1986 European Pat. Off.
196551 8/1989 Japan.

OTHER PUBLICATIONS

Gustafson, Medical and Biological Engineering, X-ray Spectrophotometry for Bone Mineral Determinations, 1974, pp. 113–117.
Kelcz, Medical Physics, Absorption-Edge Fluoroscopy Using Three-Spectrum Technique, 1976, pp. 159–168.

Primary Examiner—David P. Porta
Assistant Examiner—Kim-Kwok Chu
Attorney, Agent, or Firm—Koda and Androlia

[57] ABSTRACT

A bone mineral content measuring apparatus for obtaining the bone mineral content of an object to be examined by irradiating X-rays onto the object and measuring the X-rays which have passed through the object. An X-ray generating device generates X-rays having a continuous spectrum. The X-rays generated pass through an X-ray filter before the irradiation of the object or after the transmission of the object. The X-ray filter is composed of a substance having an X-ray absorbing characteristic with the K-absorption edge at a predetermined energy value. The X-rays which have passed through the X-ray filter and the object are detected by the X-ray detector. A data analyzer inputs the detected X-ray detection data and analyzes the bone mineral content of the object on the basis of the X-ray absorbing characteristic of the X-ray filter.

11 Claims, 10 Drawing Sheets

| FILTER | SUBSTANCE | K-ABSORPTION EDGE E(keV) | ΔE |
|---|---|---|---|
| FOR LOW ENERGY | $F_{L\alpha}$ | Gd | 50.2 | |
| | $F_{L\beta}$ | Ce | 40.4 | $45.3 \pm 4.9$ |
| FOR HIGH ENERGY | $F_{H\alpha}$ | Pb | 88.0 | |
| | $F_{H\beta}$ | Au | 80.7 | $84.4 \pm 3.7$ |

BONE MINERAL CONTENT MEASURING APPARATUS

BACKGROUND OF THE INVENTION

Field of the Invention

The present invention relates to a bone mineral content measuring apparatus for measuring the bone mineral content of an object to be examined by X rays.

Description of the Related Art

In the medical field, the bone mineral content in a living body is useful information for the diagnosis of a disease relating to a bone. The bone mineral content is used for the diagnosis of, for example, osteogenesis aberration, bone deficiency and a disease in a bone.

A general bone mineral content measuring apparatus measures a bone mineral content by using radiation. That is, by irradiating the radiation onto a living body which is an object to be examined from the outside of the living body and detecting the radiation which has passed through the living body, the bone mineral content in the living body is measured from the amount of radiation absorbed into calcium, etc., which are the main components of a bone.

A conventional bone mineral content measuring apparatus is provided with a radiation source which produces, for example, $\gamma$-rays and the bone mineral content is measured by the $\gamma$-rays generated by the radiation source.

The conventional bone mineral content measuring apparatus, however, is disadvantageous in that the maintenance and handling of the radiation source is troublesome and in that the amount of radiation is lowered with the passage of time.

As a countermeasure, a bone mineral content measuring apparatus using X-rays are proposed (see Japanese Patent Laid-Open No. 49547/1989).

This bone mineral content measuring apparatus includes an X-ray generating device for generating X-rays having a continuous spectrum (white spectrum), a monochromator for converting the X-rays generated by the X-ray generating device into X-rays having a monochromatic spectrum, and an X-ray detecting device for detecting the X-rays which have passed through the living body, and obtains the bone mineral content of the living body from the detected X-ray detection data.

As the monochromator, a diffraction grating is used.

According to this bone mineral content measuring apparatus using X-rays, it is possible to eliminate the problems caused by an X-ray radiation source and to stably measure a bone mineral content for a long term.

In this conventional bone mineral content measuring apparatus using X-rays, a bone mineral content is measured by using X-rays having a plurality of different energy values. It is therefore possible to discriminate the soft tissue from the bones in the living body in the X-ray detection data, thereby realizing the measurement of a bone mineral content without the need for a water bag which is conventionally necessary for wrapping the region to be measured.

However, the conventional bone mineral content measuring apparatus using X-rays, in which it is necessary to convert X-rays having a continuous spectrum into X-rays having a monochromatic spectrum before the living body is irradiated with the X-rays, is disadvantageous in that since the conversion for a monochromatic spectrum is difficult, the monochromator has a complicated structure.

Therefore, a bone mineral content measuring apparatus which is capable of measuring a bone mineral content without the need for complicated treatment of the X-rays having a continuous spectrum which are generated by an X-ray generating device is demanded.

In addition, in the above-described conventional bone mineral content measuring apparatus using X-rays, it is difficult to adjust the intensity of the X-rays in correspondence to the region of the living body to be measured.

Therefore, a bone mineral content measuring apparatus which is capable of measuring a bone mineral content at the optimum X-ray intensity by adjusting the intensity of the X-rays in correspondence to the region of the living body being measured is demanded.

SUMMARY OF THE INVENTION

Accordingly, it is an object of the present invention to eliminate the above-described problems in the prior art and to provide a bone mineral content measuring apparatus which is capable of measuring a bone mineral content without converting X-rays having a continuous spectrum into the X-rays having a monochromatic spectrum and which is capable of measuring a bone mineral content at the optimum X-ray intensity in correspondence to the region to be measured.

To achieve this aim, a bone mineral content measuring apparatus according to the present invention mainly comprises an X-ray generating device, an X-ray detecting device, a filtering device including at least a pair of X-ray filters and a filter switching device for switching X-ray filters, a data analyzer and a display unit.

In this structure, X-rays having a continuous spectrum are first generated by the X-ray generating device.

The X-rays which have passed through the object to be examined are detected by the X-ray detecting device.

In this case, the X-rays generated are subjected to spectrum conversion when they pass through the X-ray filter which is selected by the filter switching device before the X-rays are irradiated onto the object to be examined or after they have passed through the object.

The pair of X-ray filters are respectively composed of substances having different X-ray absorbing characteristics. In other words, there are K-absorption edges at different energy values which are approximate to each other.

Therefore, a spectrum having one peak is converted to a spectrum having two peaks with the trough in the vicinity of the K-absorption edge.

The X-ray detection data detected by the X-ray detecting device are inputted to a data analyzer.

A bone mineral content analyzing circuit provided in the data analyzer obtains the bone mineral content (BMC) of the object to be examined on the basis of the difference between the data detected by the X-rays through one X-ray filter and the data detected by the X-rays through the other X-ray filter.

The average bone mineral density (BMD) is obtained by an average bone mineral density analyzing circuit provided in the data analyzer.

The display unit displays the results of analysis.

The present invention also provides a bone mineral content measuring apparatus comprising an X-ray generating device, an X-ray detecting device, an X-ray filter constituted by a substance which has a K-absorption edge at a predetermined energy value and a data analyzer.

In this structure, the X-rays having a continuous spectrum generated by the X-ray generating device are subjected to spectrum conversion by the X-ray filter which is disposed on the irradiation side or the transmission side of the object to be examined.

In other words, the spectrum having one peak is converted into a spectrum having two peaks having the trough in the vicinity of the K-absorption edge.

The data analyzer analyzes the bone mineral content on the basis of the X-ray energy information of each X-ray detection data.

The above objects, features and advantages of the present invention will become clear from the following description of the preferred embodiments thereof, taken in conjunction with the accompanying drawings.

DESCRIPTION OF THE PREFERRED EMBODIMENTS

Embodiments of the present invention will be explained hereinunder with reference to the accompanying drawings.

First Embodiment of Bone Mineral Content Measuring Apparatus

Figure 1:
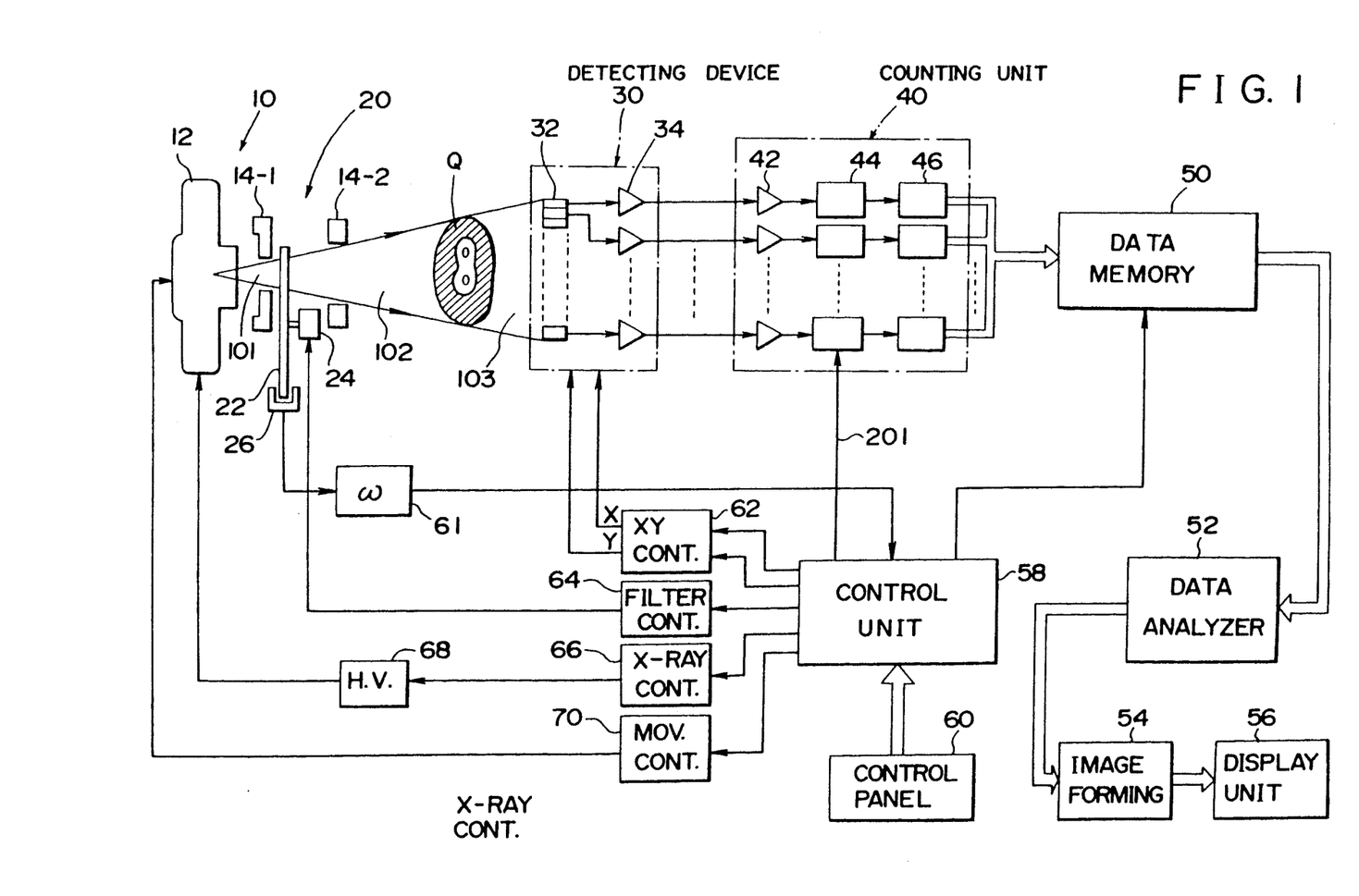
FIG. 1 is a block diagram of a first embodiment of a bone mineral content measuring apparatus according to the present invention.
Figure 2:
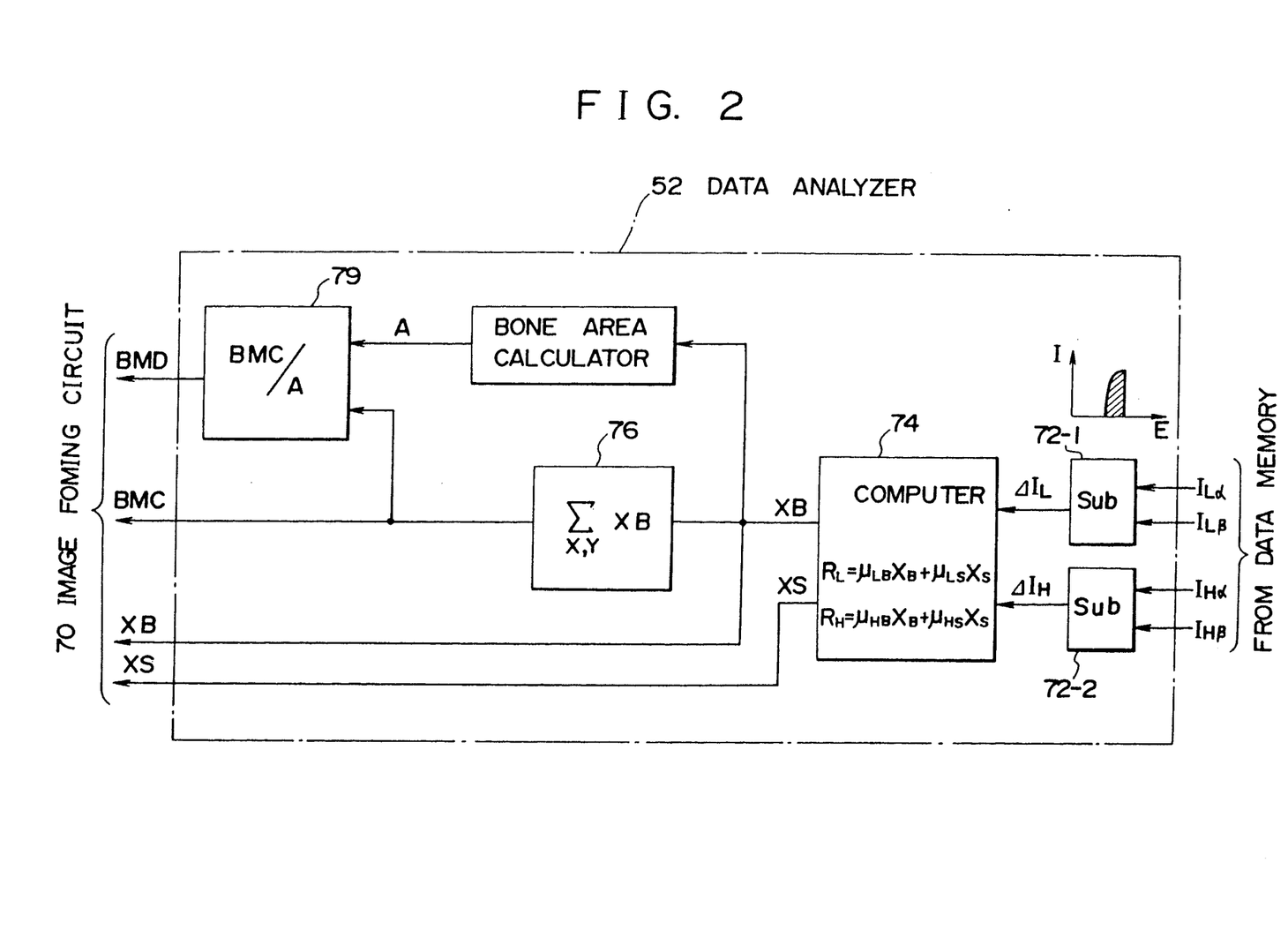
FIG. 2 is a block diagram of a data analyzer.

FIG. 1 shows a first embodiment of a bone mineral content measuring apparatus according to the present invention, and FIG. 2 shows the internal structure of a data analyzer 52.

The entire structure of the apparatus will first be explained with reference to FIG. 1.

An X-ray generating device 10 shown in the above left portion in FIG. 1 is composed of an X-ray generator 12 for generating X-rays having a continuous spectrum and two collimators 14-1, 14-2 for converging X-rays generated by the X-ray generator 12.

A filtering device 20 is provided between the X-ray generator 12 and a living body Q which is subjected to bone mineral content measurement in this embodiment. The filtering device 20 may be disposed between the living body Q and a detecting device 30 for detecting X-rays.

The filtering device 20 is provided with a plurality of X-ray filters for changing the spectrum of X-rays. The plurality of X-ray filters in combination constitute a circular filter disc 22 in this embodiment.

The filtering device 20 is also provided with a switching device 24 for switching the plurality of X-ray filters and inserting the selected X-ray filter into an X-ray beam path. The switching device 24 is composed of a motor or the like in this embodiment. The filtering device 20 (in particular, X-ray filters) will be described in detail later.

According to the above-described structure, X-rays 101 generated by the X-ray generator 12 are converged by the collimator 14-1, subjected to a predetermined spectrum conversion by one of the plurality of X-ray filters which constitute the filter disc 22, further converged by the collimator 14-2 and irradiated onto the living body Q. The X-rays pass through the living body Q while being absorbed into the bones or the like in correspondence to the amount of calcium contained therein, and are thereafter detected by the X-ray detecting device 30.

The detecting device 30 is composed of a plurality of detectors 32 and the same number of preamplifiers 34 provided for the respective detectors 32.

As the detector 32, for example, a semiconductor detector is used. In this embodiment, 80 channels of X-ray detectors are arranged one-dimensionally or two-dimensionally.

The X-rays 103 which have reached the detecting device 30 are detected by the detectors 32 and subjected to a predetermined amplification by the preamplifiers 34.

The output signals of the detecting device 30 are inputted to a counting unit 40.

The counting unit 40 is composed of a plurality of comparators 42 for comparing the detection signal with a predetermined reference signal (not shown), a plurality of gate circuits 44 for receiving the outputs of the comparators 42 and a plurality of counters 46 for counting the outputs of the corresponding gate circuit 44.

A predetermined gate signal 201 for turning ON/OFF the gates is supplied from later-described control unit 58 to the gate circuit 44.

According to this structure, the output signals from the X-ray detecting device 30 are first compared with a predetermined reference signal by the comparator 42 so that only signals above a predetermined level are selected to pass therethrough, passed through the gate circuit 44 and then counted by the counter 46.

A data memory 50 stores the counting data from the counting unit 40 for each X-ray detector 32.

The X-ray detection data stored in the data memory 50 is read out in accordance with a command from the control unit 58 and transferred to a data analyzer 52.

The data analyzer 52 calculates the bone mineral content (BMC) and the average bone mineral density (BMD) of the living body Q from the X-ray detection data supplied thereto.

The results of calculation are supplied to an image forming circuit 54 so as to form an image. This image is displayed by a display unit 56.

The data analyzer 52 also extracts the data on the soft tissue and the bone region in the living body Q, and the data corresponding to the soft tissue and the bone region are also transferred to the image forming circuit 54. The image forming circuit 54 forms a two-dimensional image of the soft tissue and the bone region which have transmitted the X-rays.

The filtering device 20 is also provided with a rotation detector 26 for detecting the rotational angle of the filter disc 22. The detection signal from the rotation detector 26 is supplied to a synchronizing circuit 61, and a synchronizing signal is supplied from the synchronizing circuit 61 to the control unit 58.

The control unit 58 opens or closes the gate circuits 44 on the basis of the supplied synchronizing signal. The opening/closing operation will be explained later together with the operation of the filter disc 22.

The control unit 58 controls the movement of the X-ray detecting device 30 in the direction of X or Y through an XY controller 62.

The control unit 58 also controls the switching (rotating) operation of the filter switching device 24 through a filter controller 64 on the basis of the synchronizing signal.

The control unit 58 also controls the generation of X-rays of the X-ray generator 12. To state this more practically, the control unit 58 controls the voltage of a high-voltage source 68 through an X-ray controller 66.

The control unit 58 further controls the movement of the X-ray generator 12 in the direction of X or Y through a movement controller 70.

A control panel 60 is connected to the control unit 58 and the operator operates the control unit 58 through the control panel 60.

The X-ray filter used in the present invention will now be explained.

In the present invention, a bone mineral content is measured by what is called a balanced filter method.

Figure 3:
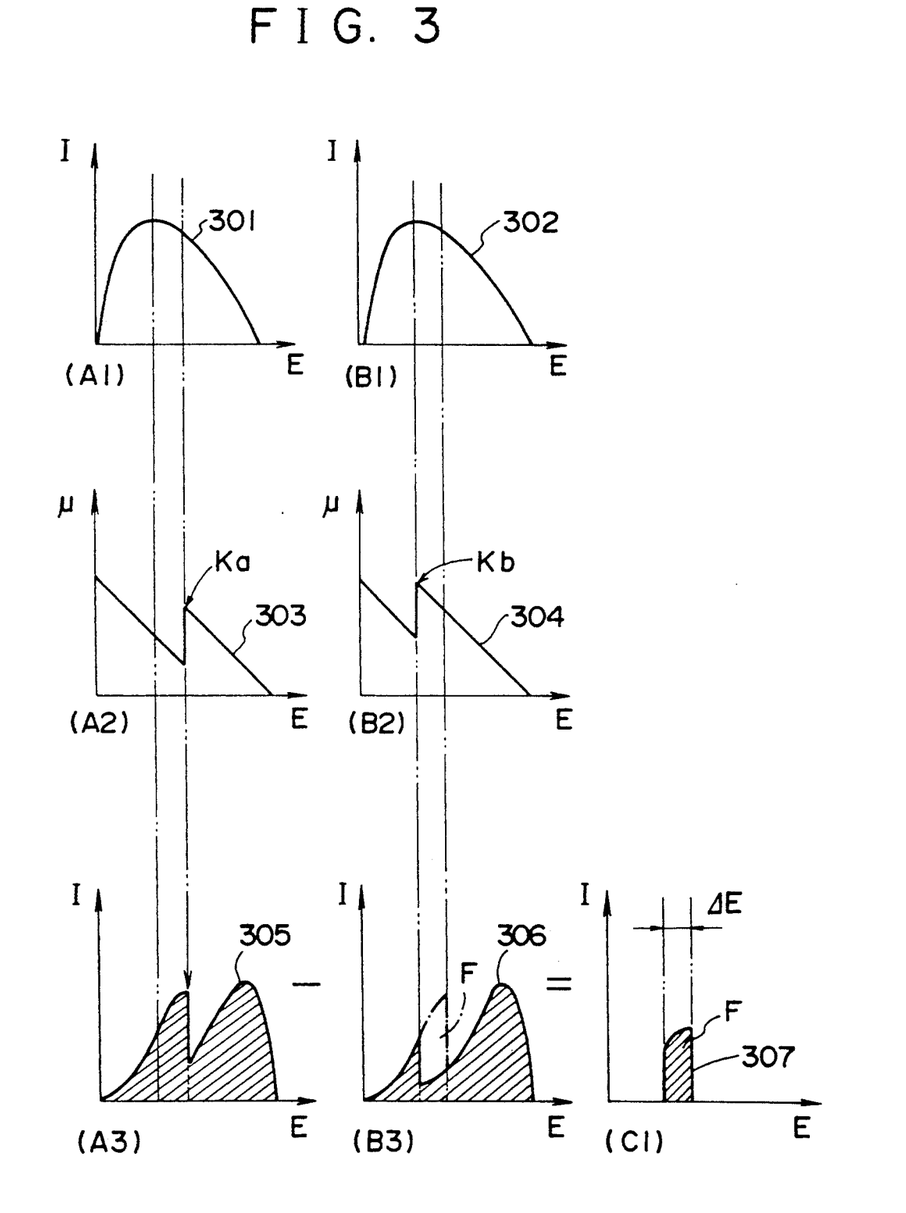
FIG. 3 is an explanatory view of a change in X-ray spectrum caused by a pair of X-ray filters.

FIG. 3 shows the principle of a method of obtaining a monochromatic spectrum from a continuous spectrum by using a pair of X-ray filters provided in a bone mineral content measuring apparatus according to the present invention.

In FIG. 3, continuous spectra 301, 302 of the X-rays generated by the X-ray generator 12 are shown in the same form of (A1) and (B1), respectively. The abscissa E represents the energy of the X-rays and the ordinate I represents the intensity of the X-rays.

In (A2) and (B2), the X-ray absorption characteristics of the pair of X-ray filters are respectively shown. The abscissa E represents the energy of X-rays and the ordinate $\mu$ represents the X-ray absorption coefficient.

The pair of X-ray filters provided in the apparatus are respectively composed of substances having K-absorption edges at different energy values. The K-absorption edge is produced by the photoelectric absorption of X-rays. This phenomenon is produced when X-rays are suddenly absorbed into the K-shell orbit due to the equality of the energy of the X-rays to the ionization energy of the electrons on the K-shell orbit.

The X-ray absorbing characteristics including the above-described K-absorption edges are indicated by the graphs 303 and 304 in (A2) and (B2). The X-ray absorbing characteristic 303 is the X-ray absorbing characteristic of one of the pair of X-ray filters and the X-ray absorbing characteristic 304 is that of the other X-ray filter.

As shown in FIG. 3, the X-ray absorbing characteristic 303 has a K-absorption edge Ka and the absorbing characteristic 304 has a K-absorption edge Kb. Ka and Kb are caused at the energies which are different from but are approximate to each other.

The X rays having the spectrum 301 shown in (A1) are absorbed into the one X-ray filter having the X-ray absorbing characteristic 303 shown in (A2), and the spectrum 301 is converted into a spectrum 305 shown in (A3).

On the other hand, the X rays having the spectrum 302 shown in (B1) are absorbed into the other X-ray filter having the X-ray absorbing characteristic 304 shown in (B2), and the spectrum 302 is converted into a spectrum 306 shown in (B3).

The difference between the spectrum 305 shown in (A3) and the spectrum 306 shown in (B3) is represented by the region F in the form of a spectrum in (C1).

In the actual bone mineral content measurement, the spectra 305 and 306 are obtained as the count values (the hatched portions in (A3) and (B3) by the counting unit 40, and the difference F is obtained from the difference between the two count values.

In this way, by irradiating X-rays having a continuous spectrum on the living body to obtain the X-ray detection data and obtaining the difference between the spectra by the above-described method, it is possible to obtain the X-ray detection data similar to that obtained by the irradiation of X-rays having a monochromatic spectrum, thereby enabling the analysis of the bone mineral content.

(A) First Example of X-Ray Filter

A first example of an X-ray filter which is applied to a bone mineral content measuring apparatus according to the present invention will now be explained.

Figure 4A:
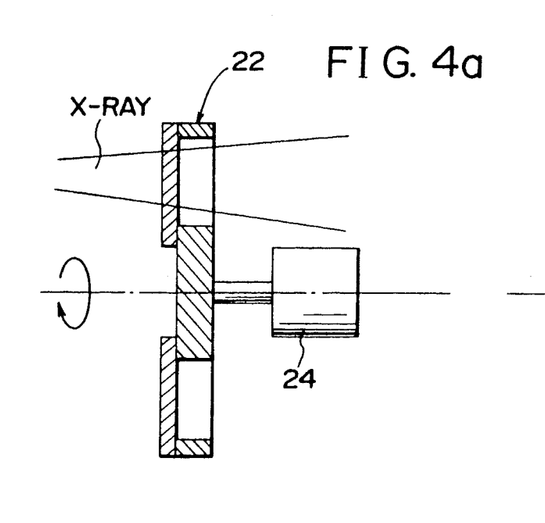
FIGS. 4a and 4b schematically show a first example of an X-ray filter.
Figure 4B:
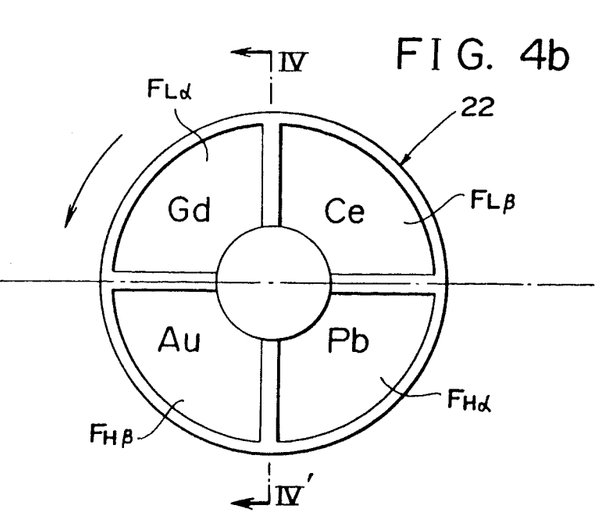

FIGS. 4a and 4b show a first example of an X-ray filter, wherein FIG. 4a is a schematic sectional view of the filter disc 22 shown in FIG. 4b, taken along the line IV—IV', and FIG. 4b is a schematic elevational view of the filter disc 22. A plurality of X-ray filters are united into one body to constitute the circular filter disc 22, as explained with reference to FIG. 1.

In FIG. 4b, the filter disc 22 is composed of four sectoral X-ray filters, namely, a pair of X-ray filters $F_{L\alpha}$, $F_{L\beta}$ for a low energy and a pair of X-ray filters $F_{H\alpha}$, $F_{H\beta}$ for a high energy.

It is in order to irradiate X-rays in the two energy regions that the pairs of X-ray filters for a high energy and low energy are provided. By this structure, it is possible to analyze the data on the soft tissue separately from the data on the bone by using the X-ray detection data in the two energy regions.

Figure 5:
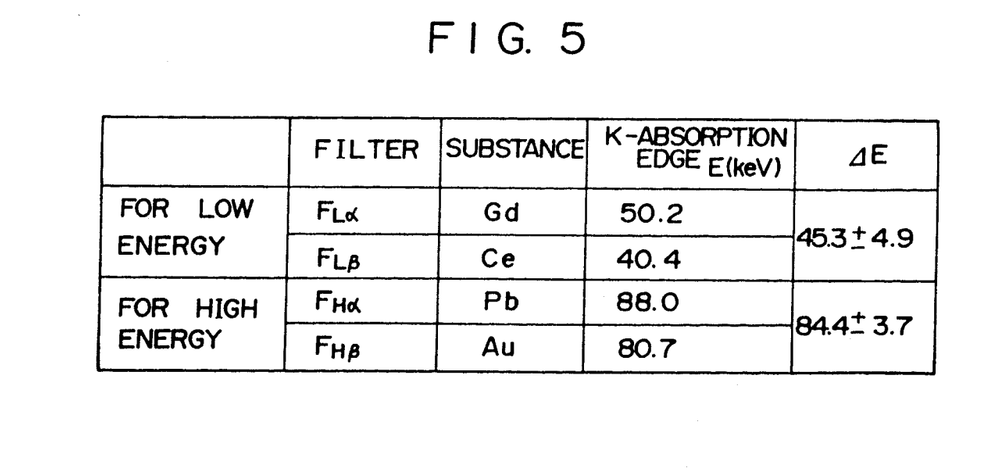
FIG. 5 is a list of the substances which constitute the first example of an X-ray filter.

FIG. 5 is a list of the substances which constitute the filter disc 22 shown in FIG. 4. For the pair of X-ray filters for a low energy, Gd (gadolinium) and Ce (cerium) are used, while for the pair of X-ray filters for a high energy, Pb (lead) and Au (gold) are used. It is naturally possible to use other substances for the X-ray filters, but it is necessary that the energy values at which K-absorption edges are produced are approximate to each other in a pair of X-ray filters.

The filter disc 22 shown in FIG. 4 is rotated by the filter switching device which is composed of, for example, a motor. By this rotation, the position on the filter disc 22 irradiated with the X-rays is continuously changed, and the spectrum of the X-rays is changed depending upon the substance of the X-ray filter.

Figure 6:
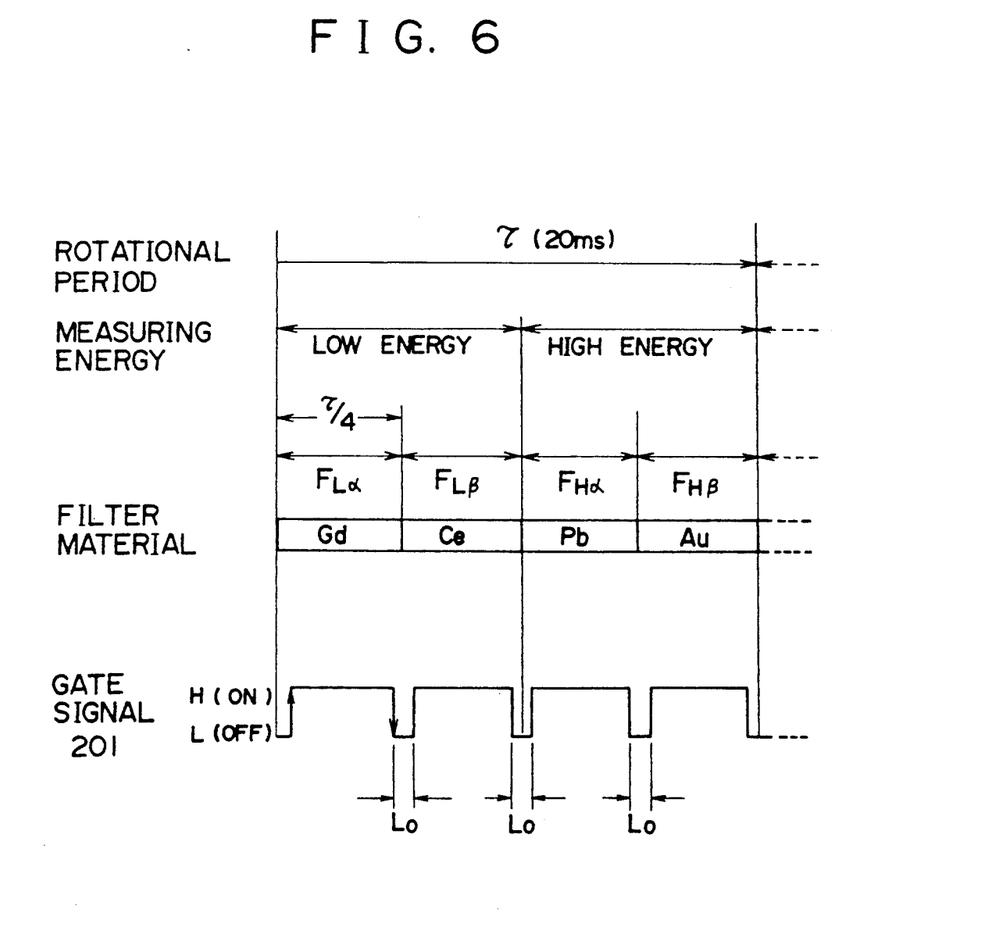
FIG. 6 is a timing chart showing the relationship between the rotation of the X-ray filter and the gate signal in the first example of an X-ray filter.

FIG. 6 shows the relationship between the rotation of the filter disc 22 and the gate signal 201.

The filter disc 22 is rotated at a rotational period $\tau$. In this embodiment, the rotational period $\tau$ is 20 ms.

Since the filter disc 22 is divided into four X-ray filters, the X-rays are transmitted through different substances at intervals of $\tau/4$. In the former half $\tau/2$ of one period $\tau$, since the pair of filters for a low energy are used, measurement is carried out by the X-rays having a low energy, while in the latter half $\tau/2$ of one period $\tau$, since the pair of filters for a high energy are used, measurement is carried out by the X-rays having a high energy.

The gate signal 201 is supplied from the control unit 58 to the gate circuit 44 in synchronoization with the switching of the X-ray filters. The gate circuit 44 is turned on with the rise of the gate signal 201 and turned off with the fall of the gate signal 201.

This is because the operation for acquisition of the X-ray detection data is suspended at the time of switching the X-ray filters. The gate signal 201 falls to $L_0$ in about 1 ms during the operation of switching the X-ray filters, as shown in FIG. 6, and the gate circuit 44 is turned off in this period $L_0$.

The filter disc 22 constantly rotates at a constant angular speed during the measurement of a bone mineral content, while the filters are continuously switched for scanning the living body Q with the X-ray beam.

(B) Second Embodiment of X-Ray Filter

Figure 7A:
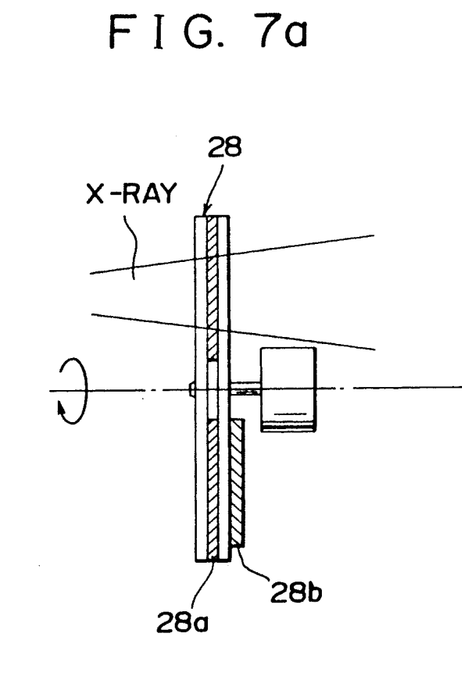
FIG. 7a and 7b schematically shows a second example of an X-ray filter.
Figure 7B:
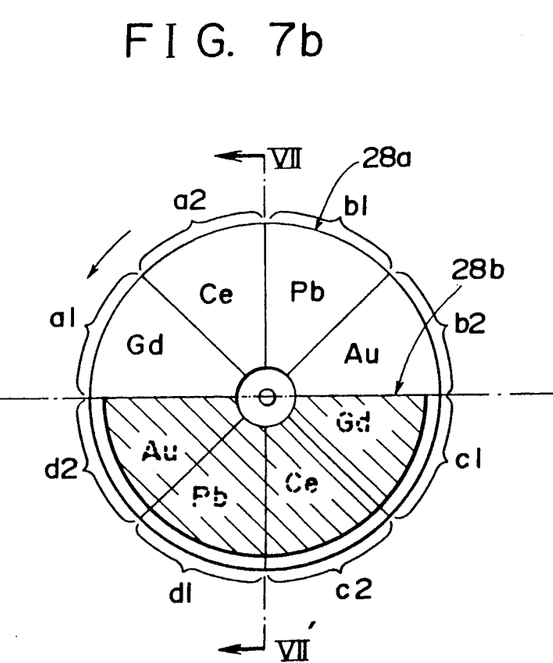

FIG. 7 shows a second example of an X-ray filter which is applied to a bone mineral content measuring apparatus according to the present invention, wherein FIG. 7a is a schematic sectional view of a filter disc 28 shown in FIG. 7b, taken along the line VII-VII', and FIG. 7b is a schematic elevational view of the filter disc 28. A plurality of filters are united into one body to constitute the circular filter disc 28.

The filter disc 28 is composed of four pairs of X-ray filters, namely, a pair of X-ray filters a1, a2 for a high X-ray intensity and a low energy, a pair of X-ray filters b1, b2 for a high X-ray intensity and a high energy, a pair of X-ray filters c1, c2 for a low X-ray intensity and a low energy and a pair of X-ray filters d1, d2 for a low X-ray intensity and a high energy.

In other words, the filter disc 28 is composed of a combination of X-ray filters which corresponds to all the combinations of the intensity and the energy of X-rays.

For example, it is possible to measure by the irradiation of X-rays having a low intensity the bone mineral content of a region which does not require X-rays to have a very high intensity such as the arm region. On the other hand, with respect to the region which requires X-rays to have a comparatively high intensity such as the abdominal region, the bone mineral content is measured by the irradiation of X-rays having a high intensity.

Thus, this example is advantageous in that the bone mineral content measurement is enabled with X-rays having an appropriate intensity in correspondence to the region to be measured. Although the intensity of X-rays are divided into two in this example, it may naturally be divided into three or four.

As shown in FIGS. 7a and 7b, with the filter disc 28, the same substances as those shown in FIG. 4 are used for the filters a1, a2, b1 and b2, respectively, and the X-ray filters c1, c2, d1 and d2, are produced by overlaying the respective filter substances shown in FIG. 4 with an X-ray attenuating layer.

As shown in FIG. 7a, the respective sectoral filter substances are united into one body so as to form a discoidal first filter layer 28a, and the first filter layer 28a is further overlaid with a semicircular second filter layer 28b consisting of an X-ray attenuating substance.

As the X-ray attenuating substance, copper (Cu), brass (Cu+Zn) or the like is preferably used.

Although the intensities of the X-rays are switched by overlaying the circular first filter layer 28a with the semicircular second filter layer 28b in this embodiment, the method of switching the intensities of the X-rays is not restricted thereto. For example, two kinds of X-ray filters having different thicknesses may be provided so as to switch the intensities of the X-rays. Alternatively, an X-ray attenuating filter may be disposed independently in the X-ray beam path.

In this example, the thicknesses of the Gd, Ce and Pb filters are 0.512 mm, 0.756 mm and 0.685 mm, respectively, and the thickness of the X-ray attenuating layer is about 1.0 mm.

It is also preferable that the thicknesses of the Gd, Ce and Pb filters are 0.256 mm, 0.378 mm and 0.852 mm, respectively, and the X-ray attenuating layer is a composition of copper having a thickness of 0.2 mm and brass having a thickness of 0.8 mm.

Figure 8:
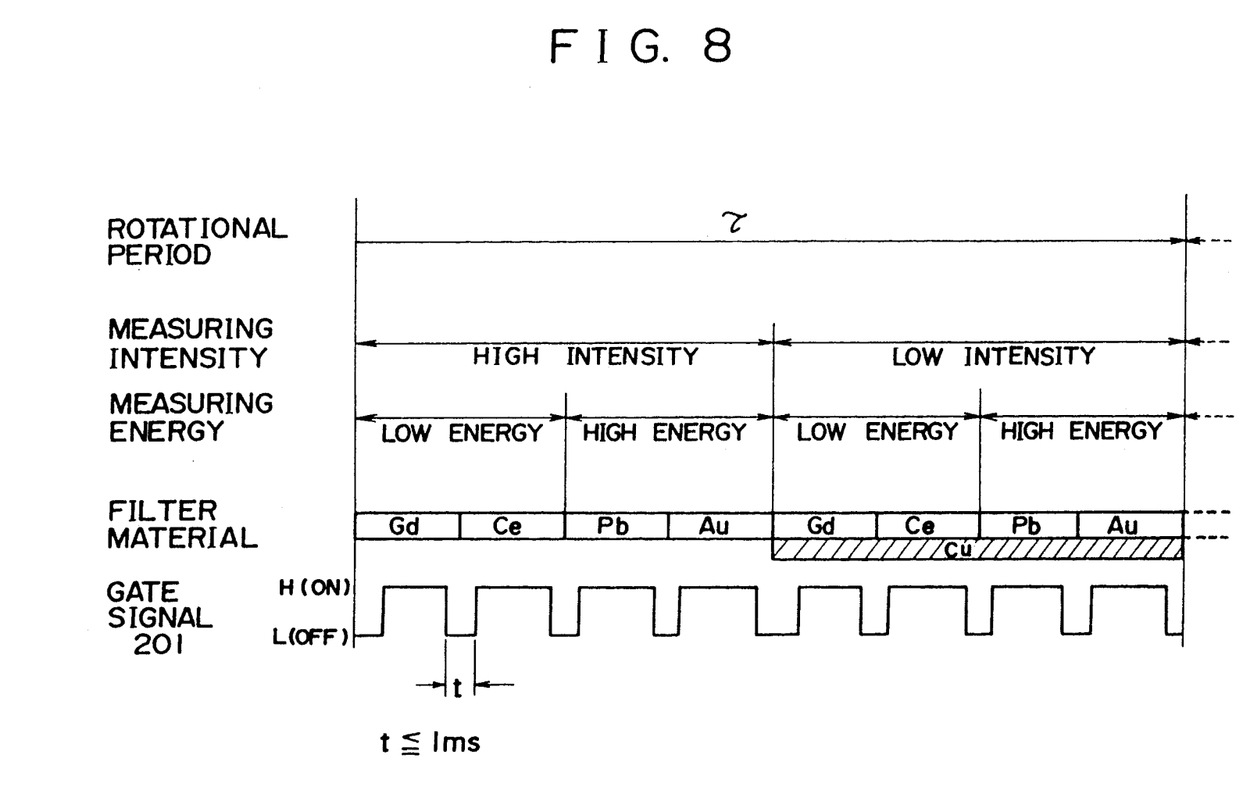
FIG. 8 is a timing chart showing the relationship between the rotation of the X-ray filter and the gate signal in the second example of an X-ray filter.

FIG. 8 shows the relationship between the rotation of the filter disc 28 and the gate signal 201.

In the former half $\tau/2$ of one rotational period $\tau$, the two pairs of filters for a high X-ray intensity are used, while in the latter half $\tau/2$ of one period $\tau$, the two pairs of filters for a low X-ray intensity are used.

At intervals of $\tau/4$, a pair of X-ray filters for a high energy and a pair of X-ray filters for a low energy are switched over each other, and at intervals of $\tau/8$, the current X-ray filter is switched over the subsequent X-ray filter.

The gate signal 201 supplied from the control unit 58 to the gate circuit 44 forms a wave form in synchronization with the switching of the filters. In this way, the gate signal 201 prevents the border of the X-ray filters from being irradiated with the X-ray beam at the time of switching the filters which would lead to the deterioration of the accuracy of the X-ray detection data.

The second example of the X-ray filter is rotated, for example, at a rotational period of 40 ms for the measurement of the whole body and at a rotational period of 400 ms for the measurement of the bone mineral content of the lumbar or the cerebrum. It is naturally preferable to vary the rotational period in accordance with the region of the living body to be measured.

The X-ray filter is discoidal in the above examples, but the configuration is naturally not restricted thereto and may be different.

These examples are advantageous in that since the sectoral X-ray filters are united into one body so as to form a filter disc, the filters can be switched easily, swiftly, continuously and smoothly by the rotation of the filter disc.

(C) Structure of Data Analyzer 52

FIG. 2 shows a block diagram of the data analyzer 52 shown in FIG. 1.

The X-ray detection data are inputted from the data memory 50 to two subtracters 72-1, 72-2. Data $I_{L\alpha}$, $I_{L\beta}$ obtained by using the pair of X-ray filters for a low energy are inputted to the subtracter 72-1, and data $I_{H\alpha}$, $I_{H\beta}$ obtained by using the pair of X-ray filters for a high energy are inputted to the subtracter 72-2. It is naturally possible to subsequently obtain the difference between the data from the measurement with a high energy and the difference between the data from the measurement with a low energy by one subtracter.

The subtracters 72-1, 72-2 execute the following calculations:

$$\Delta I_L = I_{L\alpha} - I_{L\beta}$$

$$\Delta I_H = I_{H\alpha} - I_{H\beta} \quad (1)$$

wherein $\Delta I_L$ and $\Delta I_H$ are the above described differences. These differences represent the region F shown in (C1) of FIG. 3.

The differences $\Delta I_L$ and $\Delta I_H$ are inputted to a computer 74.

The computer 74 solves the following simultaneous equations to obtain the thickness $X_B$ of the bone and the thickness $X_S$ of the soft tissue along the X-ray beam:

$$R_L = \mu_{LB} \cdot X_B + \mu_{LS} \cdot X_S$$

$$R_H = \mu_{HB} \cdot X_B + \mu_{HS} \cdot X_S \quad (2)$$

wherein $$R_L = \ln(\Delta I_{L0}/\Delta I_L)$$

$$R_H = \ln(\Delta I_{H0}/\Delta I_H) \quad (3)$$

wherein $\Delta I_{L0}$ and $\Delta I_{H0}$ are the initial differences between the spectra of the X-rays having a low energy and between the spectra of the X-rays having a high energy, respectively, which are not transmitted through the living body.

In the above equations, $\mu_{LB}$, $\mu_{LS}$, $\mu_{HB}$ and $\mu_{HS}$ are the X-ray absorption coefficients (cm$^{-1}$) of the bone and the soft tissue, respectively, with respect to X-rays having a high energy and a low energy, respectively.

By solving the above simultaneous equations, the thickness $X_B$(cm) of the bone and the thickness $X_S$(cm) of the soft tissue are obtained.

$X_B$ obtained is inputted to a bone mineral content analyzing circuit 76 and $X_B$ in the direction of X and $X_B$ in the direction of Y are accumulated. The accumulated value is multiplied by a predetermined coefficient to obtain the bone mineral content (BMC), as follows:

$$BMC = \Sigma X B \cdot \rho B \cdot \delta S \text{ (g)} \quad (4)$$

wherein $\rho B$ represents the density (g/cm$^3$) of the bone and $\delta S$ represents the element area (cm$^2$).

In this embodiment, since 80 channels of X-ray detectors 32 are provided, the accumulation for 80 channels is executed.

The output $X_B$ of the computer 74 is inputted to a bone area calculator 78.

The bone area calculator 78 obtains the area of the bone by extracting the data on the X-rays which have passed through the bone region in the living body from the X-ray detection data. The X-ray detection data from each channel of the detector 32 is compared with a predetermined threshold value and the area A of the bone is obtained from the number of the channels which have the X-ray detection data exceeding the threshold value.

Both the data on the area A from the bone area calculator 78 and the data on the bone mineral content BMC from the bone mineral content analyzing circuit 76 are inputted to an average bone mineral density analyzing circuit 79.

The average bone mineral density circuit 79 obtains the average bone mineral density BMD by dividing the bone mineral content BMC by the bone area A obtained in the above described way.

The thus-obtained BMD, BMC, $X_B$ and $X_S$ are supplied to the image forming circuit 54 shown in FIG. 1.

The image forming circuit 54 forms a two-dimensional image of the living body which has transmitted the X-rays by using $X_B$ and $X_S$. For example, it is preferable to express the bone mineral content of each region by a hue and display an image obtained by the composition of each region.

As described above, according to a bone mineral content measuring apparatus of this embodiment, since X-ray filters having X-ray absorbing characteristics with the K-absorption edges at different energy values are used, it is possible to measure a bone mineral content easily without converting the continuous spectrum of the X-rays generated by the X-ray generating device into a monochromatic spectrum.

Since it is possible to measure a bone mineral content with an appropriate intensity of the X-rays in correspondence to the region to be measured by using a plurality of X-ray filters having different transmission intensities of the X-rays, the measurement with a high accuracy is enabled.

In addition, since a plurality of sectoral X-ray filters constitute a filter disc, the operation of switching the X-ray filters is facilitated and it is possible to scan the living body with the X-ray beam while continuously switching the X-ray filters.

Thus, it is possible to select the optimum X-ray detection data from the stored X-ray detection data in correspondence to the region to be measured and to obtain the bone mineral content with a high accuracy.

Second Embodiment of Bone Mineral Content Measuring Apparatus

Figure 9:
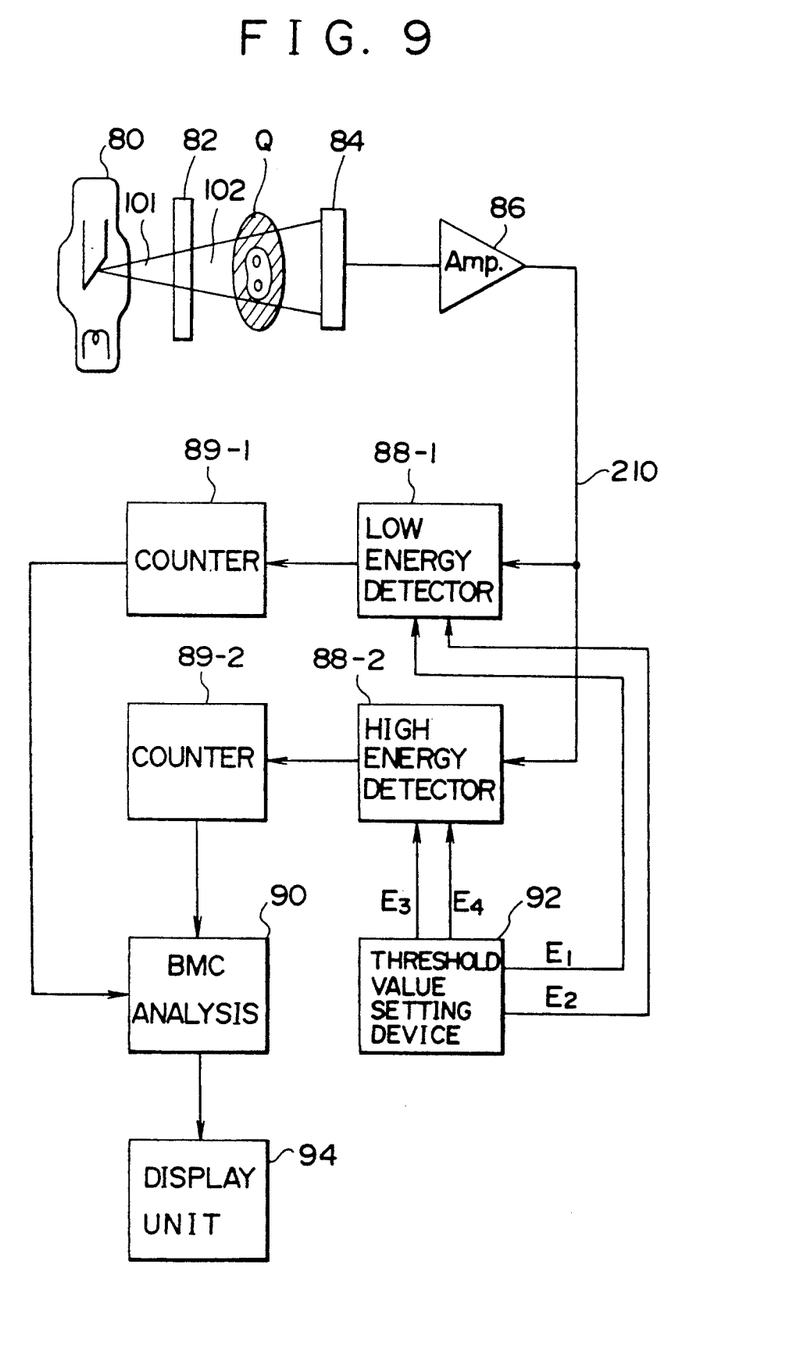
FIG. 9 is a block diagram of a second embodiment of a bone mineral content measuring apparatus according to the present invention.

FIG. 9 shows a second embodiment of a bone mineral content measuring apparatus according to the present invention.

An X-ray generating device 80 generates X-rays having a continuous spectrum.

The X-rays generated are subjected to a predetermined spectrum conversion by an X-ray filter 82.

The X-ray filter 82 is composed of a substance having an X-ray absorbing characteristic with the K-absorption edge at a predetermined energy value.

The X-rays which have passed through the X-ray filter 82 are absorbed into the living body Q in correspondence to the bone mineral content and thereafter detected by an X-ray detecting device 84.

The X-ray detecting device 84 is composed of, for example, semiconductor detectors which are arranged one-dimensionally or two-dimensionally.

The operation of the X-ray filter 82 will be explained with reference to FIG. 10.

Figure 10:
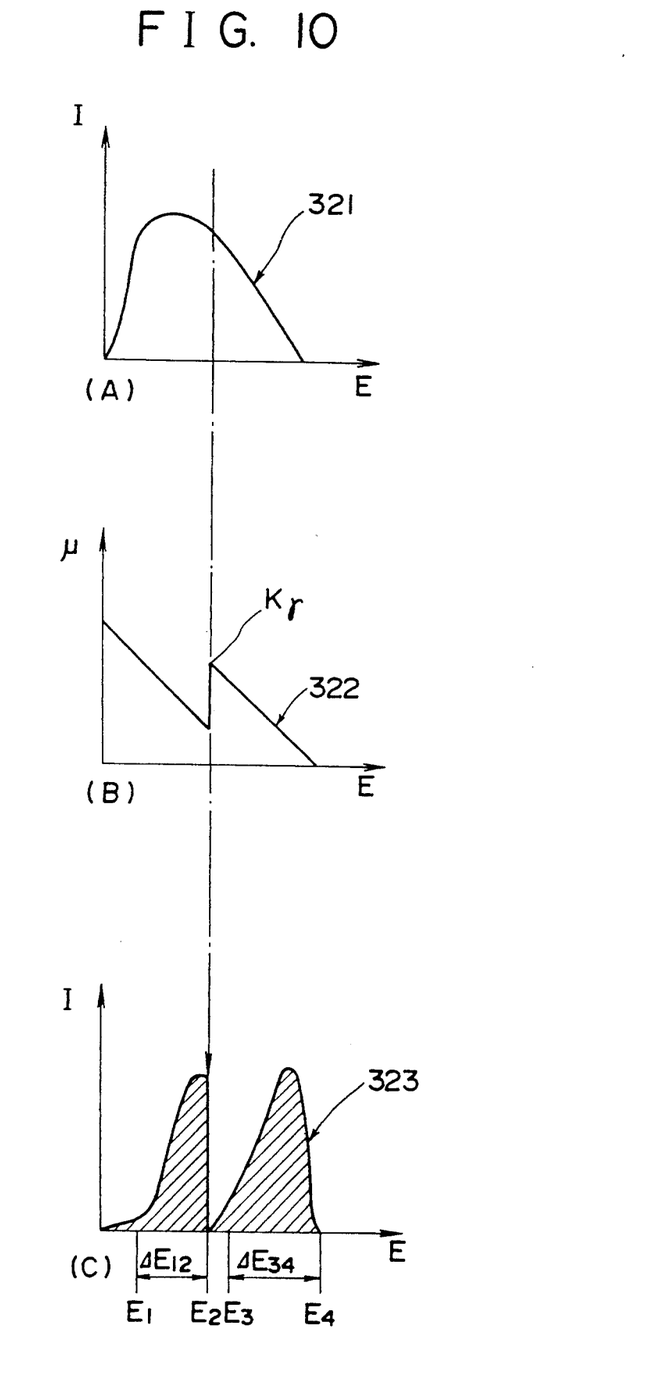
FIG. 10 is an explanatory view of the operation of an X-ray filter.

In FIG. 10, the spectrum 321 of the X-rays generated by the X-ray generating device 80 is shown in (A). The abscissa E represents the energy of the X-rays and the ordinate I represents the intensity of the X-rays.

The X-rays having the spectrum 321 are subjected to a predetermined absorption by the X-ray filter 82.

The X-ray absorbing characteristic 322 of the X-ray filter 82 is shown in (B). The abscissa E represents the energy of the X-rays and the ordinate $\mu$ represents the X-ray absorption coefficient.

As described above, the X-ray filter 82 is composed of a substance having an X-ray absorbing characteristic with the K-absorption edge at a predetermined energy value. The K-absorption edge $K_\gamma$ is shown in (B).

According to this X-ray filter 82, the spectrum 321 having one peak is converted to a spectrum 323 having two peaks with the trough in the vicinity of the K-absorption edge $K_\gamma$, as shown in (C).

In this embodiment, the bone mineral content is measured by using the characteristic of the spectrum having two peaks.

In other words, the measurement of a bone mineral content similar to the measurement of a bone mineral content using two X-rays having monochromatic spectra and different energies is carried out by using the spectrum 323 having two peaks.

Returning to FIG. 9, the detection signal from the X-ray detecting device 84 is inputted to a preamplifier 86 for a predetermined amplification.

The amplified detection signal is supplied to a low energy detector 88-1 and a high energy detector 88-2.

Predetermined threshold value signals $E_1$, $E_2$ are supplied from a threshold value setting device 92 to the low energy detector 88-1 and predetermined threshold value signals $E_3$, $E_4$ are supplied from the threshold value setting device 92 to the high energy detector 88-2.

By using these energy detectors 88, it is possible to extract the detection signals within the two specified energy regions shown in (C) of FIG. 10, namely, a specified low energy region $\Delta E_{12}$ and a specified high energy region $\Delta E_{34}$.

Figure 11:
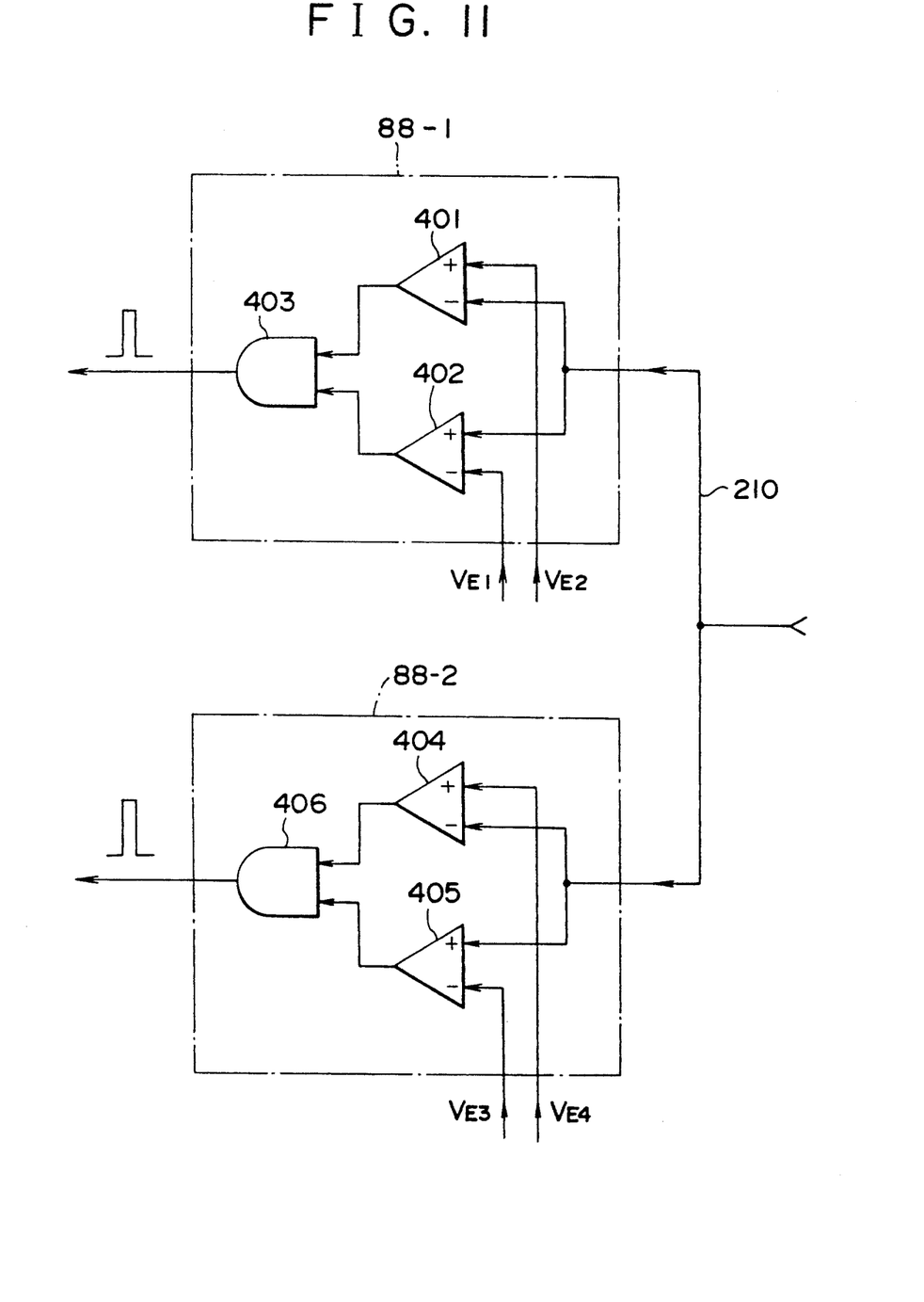
FIG. 11 is a circuit diagram of energy detectors.

FIG. 11 is a circuit diagram of the low energy detector 88-1 and the high energy detector 88-2.

The low energy detector 88-1 is composed of two comparators 401, 402 for the upper limit and the lower limit, respectively, for comparing a detection signal 210 with the threshold signals and an AND gate 403 for inputting the outputs of the two comparators 401, 402.

The high energy detector 88-2 is composed of two comparators 404, 405 and an AND gate 406, in the same way as in the low energy detector 88-1.

By this structure, the detection signals within the specified low energy region $\Delta E_{12}$ and the specified high energy region $\Delta E_{34}$ are extracted.

The output signals from the respective energy detectors 88 are supplied to counters 89-1 and 89-2 for counting.

A bone mineral content analyzing circuit 90 inputs the outputs of the counters 89-1, 89-2, and calculates the bone mineral content on the basis of the count value in the specified low energy region $\Delta E_{12}$ and the count value in the specified high energy region $\Delta E_{34}$.

The bone mineral content obtained is input to a display unit 94 for a predetermined display.

As described above, according to the bone mineral content measuring apparatus of this embodiment, since the X-ray filter is composed of a substance having the K-absorption edge at a predetermined energy value, it is possible to measure the bone mineral content in the same way as in the case of using two X-rays having monochromatic spectra. Thus, it is possible to realize a bone mineral content measuring apparatus having a simple structure.

This embodiment is advantageous especially in that since the measurement with X-rays in a low energy region and the measurement with X-rays in a high energy region can be simultaneously carried out, the swift bone mineral content measurement is enabled.

The position of the X-ray filter 82 between the X-ray generating device 80 and the living body Q is not essential, and the X-ray filter 82 may be disposed between the living body Q and the X-ray detecting device 84.

It is also preferable to arrange a plurality of X-ray filters having K-absorption edges at different energy values and switch the filters by a filter switching device. In this case, the substances such as those shown in FIG. 5 are used for the X-ray filters.

While there has been described what is at present considered to be preferred embodiments of the invention, it will be understood that various modifications may be made thereto, and it is intended that the appended claims cover all such modifications as fall within the true spirit and scope of the invention.

What is claimed is:

1. A bone mineral content measuring apparatus comprising:

(a) an X-ray generating device for generating X-rays having a continuous spectrum;

(b) an X-ray detecting device for detecting the X-rays which have passed through an object to be examined;

(c) a filtering device including at least one pair of X-ray filters which are switched over each other and provided in an X-ray beam path between said X-ray generating device and said X-ray detecting device, and a filter switching device for switching said X-ray filters, said pair of X-ray filters being composed of substances having different X-ray absorbing characteristics with K-absorption edges at different energy values which are approximately equal to each other;

(d) a data analyzer for inputting the X-ray detection data from said X-ray detecting device and analyzing said data, said data analyzer including a spectrum subtracter and a bone mineral content analyzing circuit, said spectrum subtracter calculating the difference data between the X-ray detection data obtained by using one of said pair of X-ray filters and the X-ray detection data obtained by using the other of said pair of X-ray filters, said difference data being equivalent to data obtained by using a monochromatic spectrum, and said bone mineral content analyzing circuit providing the bone mineral content of said object on the basis of said difference data; and (e) a display unit for displaying the result of analysis of said data analyzer.

2. A bone mineral content measuring apparatus according to claim 1, wherein said filtering device includes:

a pair of X-ray filters for a low energy which are composed of substances having the K-absorption edges in a low energy region; and a pair of X-ray filters for a high energy which are composed of substances having the K-absorption edges in a high energy region.

3. A bone mineral content measuring apparatus according to claim 2, wherein each of said X-ray filters is formed into a sector having a predetermined angle and a combination of all the pairs of X-ray filters constitutes a circular filter disc; and said filter switching device switches said X-ray filters by the rotation of said filter disc.

4. A bone mineral content measuring apparatus according to claim 3, wherein said filter disc is rotated at a constant angular velocity for bone mineral content measurement.

5. A bone mineral content measuring apparatus according to claim 3, wherein one of said pair of X-ray filters for a low energy is composed of Gd, the other being composed of Ce; and one of said pair of X-ray filters for a high energy is composed of Pb, the other being composed of Au.

6. A bone mineral content measuring apparatus according to claim 1, wherein said filtering device includes:

a first pair of X-ray filters for a low energy which are composed of substances having the K-absorption edges in a low energy region;

a second pair of X-ray filters for a low energy which are composed of said first pair of X-ray filters for a low energy overlaid with an X-ray attenuating substance having a predetermined thickness;

a first pair of X-ray filters for a high energy which are composed of substances having the K-absorption edges in a high energy region; and a second pair of X-ray filters for a high energy which are composed of said first pair of X-ray filters for a high energy overlaid with an X-ray attenuating substance having a predetermined thickness.

7. A bone mineral content measuring apparatus according to claim 6, wherein each of said X-ray filters is formed into a sector having a predetermined angle and a combination of all the pairs of X-ray filters constitutes a circular filter disc; and said filter switching device switches said X-ray filters by the rotation of said filter disc.

8. A bone mineral content measuring apparatus according to claim 7, wherein said filter disc is rotated at a constant angular velocity for bone mineral content measurement.

9. A bone mineral content measuring apparatus according to claim 7, wherein one of said first pair of X-ray filters for a low energy is composed of Gd, the other being composed of Ce;

one of said first pair of X-ray filters for a high energy is composed of Pb, the other being composed of Au; and said X-ray attenuating substance contains at least one selected from the group consisting of copper and brass.

10. A bone mineral content measuring apparatus according to claims 3 or 7, wherein said data analyzer includes an average bone mineral density analyzing circuit for obtaining an average bone mineral density.

11. A bone mineral content measuring apparatus according to claims 3 or 7, wherein said filtering device is disposed between said X-ray generating device and said object to be examined.

* * * * *